(12) United States Patent
Atkinson

(10) Patent No.: US 7,316,166 B2
(45) Date of Patent: Jan. 8, 2008

(54) METHOD AND SYSTEM FOR ANALYZING MULTI-PHASE MIXTURES

(75) Inventor: Ian Atkinson, Ely (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 11/609,167

(22) Filed: Dec. 11, 2006

(65) Prior Publication Data

US 2007/0144268 A1    Jun. 28, 2007

(30) Foreign Application Priority Data

Dec. 17, 2005  (GB)  ................................. 0525722.5

(51) Int. Cl.
*G01F 1/44* (2006.01)
(52) U.S. Cl. .................................. 73/861.63
(58) Field of Classification Search ............. 73/861.63; 378/52–54; 250/269.1, 364, 358.1
See application file for complete search history.

(56) References Cited

U.S. PATENT DOCUMENTS

| | | | |
|---|---|---|---|
| 4,788,852 A | 12/1988 | Martin et al. | |
| 4,856,344 A | 8/1989 | Hunt | |
| 5,783,828 A * | 7/1998 | Pacenti et al. | ............... 250/364 |
| 6,097,786 A * | 8/2000 | Groves et al. | ................. 378/53 |
| 6,265,713 B1 | 7/2001 | Berard et al. | |
| 6,286,367 B1 | 9/2001 | Segeral | |
| 6,776,054 B1 | 8/2004 | Stephenson et al. | |

FOREIGN PATENT DOCUMENTS

| | | |
|---|---|---|
| GB | 2 088 050 A | 6/1982 |
| GB | 2 316 167 A | 2/1998 |
| JP | 61-128145 A | 6/1986 |
| WO | 97/42493 A1 | 11/1997 |
| WO | 01/25762 A1 | 4/2001 |

* cited by examiner

*Primary Examiner*—Jewel Thompson
(74) *Attorney, Agent, or Firm*—Vincent Loccisano; Jody Lynn DeStefanis; Steven Gahlings

(57) ABSTRACT

A method and apparatus is disclosed for identifying changes in composition in a flow containing an oil/hydrocarbon gas fluid mixture, including a measurement of the respective holdups of any two of the gas, oil and water; and measurements to determine attenuation or scattering of high energy photons passing through the mixture; and combining holdup measurements and attenuation or scattering measurements to detect the presence or concentration of a hetero-component in the mixture.

8 Claims, 3 Drawing Sheets

METHOD AND SYSTEM FOR ANALYZING MULTI-PHASE MIXTURES

CROSS-REFERENCE TO RELATED APPLICATION

This application claims the benefits of priority from Application Number 0525722.5, entitled "METHOD AND SYSTEM FOR ANALYZING MULTI-PHASE MIXTURES," filed in the United Kingdom on Dec. 17, 2005.

FIELD OF THE INVENTION

The present invention relates to the field of flow meters for multiphase mixtures, in particular, flow meters for oil and water mixtures in hydrocarbon boreholes. More specifically, the invention pertains to the analysis of the composition of multiphase mixtures.

BACKGROUND OF THE INVENTION

The measurement of oil and water flow rate in each producing zone of an oil well is important to the monitoring and control of fluid movement in the well and reservoir. In addition to a flow meter, each zone may have a valve to control the fluid inlet from that zone. By monitoring flow rates of oil and water from each zone and reducing flow from those zones producing the highest water cut (i.e., ratio of water flow rate to total flow rate), the water production of the entire well can be controlled. This, in addition, allows the reservoir oil to be swept more completely during the life of the well.

Typically, flow meters determine the holdup, i.e. the volume fraction of the gas, oil or water phase, and the velocity of the gas phase, the oil phase, or the water phase. The flow rate of water is then determined from the product of water holdup $\alpha_w$, the pipe area A, and the velocity of water $U_w$. An analogous relation holds for oil and gas flow rate. Other parameters of interest such as the slip ratio of velocities of the different phases, the gas-liquid ratio (GLR), the water-liquid ratio (wlr) and the gas-oil ratio (GOR) may be determined in the same multiphase measurement.

According to known methods, the holdups may be measured using a gamma-ray, dual energy fraction meter. Based on knowledge of the chemical composition of the gas, oil and water, such a meter conventionally measures the gas holdup, and one of the water or oil holdup (the requirement for the sum of all three holdups to equal one allows the other of the water or oil holdup to be calculated). That is, three compositional inputs allow the determination of two holdup outputs.

A number of methods of flow measurement are known such as capacitance, microwave, acoustic methods are know and extensively described in the relevant literature. Some of which use direct measurement or determine velocities through secondary measurements such as correlation measurements or are exploiting the Doppler effect.

Another method of velocity measurement uses a Venturi. In single phase flow, a Venturi generally obeys the Bernoulli equation which relates volumetric flow rate Q to fluid density ρ and pressure drop from the inlet to the throat of the Venturi.

A common method to determine the holdup in a flow of gas, oil and water is to measure the average density of the fluid. Since oil at downhole pressure and temperature typically has a density which is smaller than that of water (around 0.7 g/cm³ compared to 1.0 g/cm³), and the gas density even smaller, the respective holdups $\alpha_o$, $\alpha_w$ and $\alpha_g$ can be determined proportionately from the mixture density using for example the known densities of the components. For that purpose modern densitometers use a dual energy gamma-ray beam probing the absorption or scattering of high energy photons at two different energy levels, the so-called high-energy and low-energy beam.

Examples of the Venturi based multiphase flowmeters are described in the U.S. Pat. Nos. 4,856,344; 6,776,054; 6,265,713 and 6,286,367, which are hereby incorporated by reference, the latter two references relating to flow meter devices comprising a Venturi meter and a gamma-ray, dual energy fraction meter. A flow meter device comprising a Venturi meter and a gamma-ray, dual energy fraction meter is commercially available from Schlumberger (RTM).

SUMMARY OF THE INVENTION

The present invention provides a method for identifying changes in composition in a flow containing an oil/hydrocarbon gas fluid mixture. The fluid mixture may also contain water.

In accordance with an aspect of the invention, the method include the steps of measuring the respective holdups of any two of the gas, oil and water (but preferably the gas and the oil); measuring the density of the fluid mixture using high energy photon beams; and identifying compositional changes in the fluid mixture from the measured holdups and attenuation, absorption or scattering of the photon beam as it passes through the fluid.

Based on initial or independent knowledge of the chemical composition of the gas, oil and water, a meter conventionally measuring the gas holdup, and one of the water or oil holdup (the requirement for the sum of all three holdups to equal one allows the other of the water or oil holdup to be calculated) allows the determination of the presence of a hetero component in the fluid mixture.

The holdups may be measured using a Venturi meter. Preferably, the fluid mixture is hydrocarbon well production fluid and the hetero-component is preferably an element or molecule not present in the "pure" three phases of mixture. Those phases are water, hydrocarbon gas and hydrocarbon liquid.

The identified compositional change may be a change in the amount of hydrogensulfide (H2S) in the fluid mixture. Such H2S may be contained in the gas and/or in the liquid phase.

The identified compositional change may be a change in water salinity.

Preferably the water-liquid ratio of the fluid mixture is known, and more preferably it is zero. A dual energy fraction meter, if used, may be calibrated for the known water-liquid ratio.

Also provided by the present invention is an apparatus for performing the above method. The apparatus may comprise a x-ray orgamma-ray, dual energy fraction meter, and a Venturi meter. It may comprise a computer system for identifying changes in composition (e.g. changes in H₂S content) of the fluid mixture from the measured holdups and the flow rate.

U.S. Pat. Nos. 6,265,713 and 6,286,367, as referred to above, are incorporated herein to provide further details of known flowmeters using methods based on Venturi-type measurements.

The known flowmeters may be modified for the purpose of the present invention by the use of more than one photon beam with a peak energy in the range of 10 keV to 80 keV.

BRIEF DESCRIPTION OF THE DRAWINGS

FIGS. 2A, 2B are showing standard mass attenuation curves in dependence of the photon energy for water, a water/salt solution, methane, methane with hydrogen sulfate, a light hydrocarbon oil, and the same with hydrogen sulfate, wherein FIG. 2B shows a magnified view of the low energy part of FIG. 2A.

DETAILED DESCRIPTION OF THE INVENTION

Figure 1:
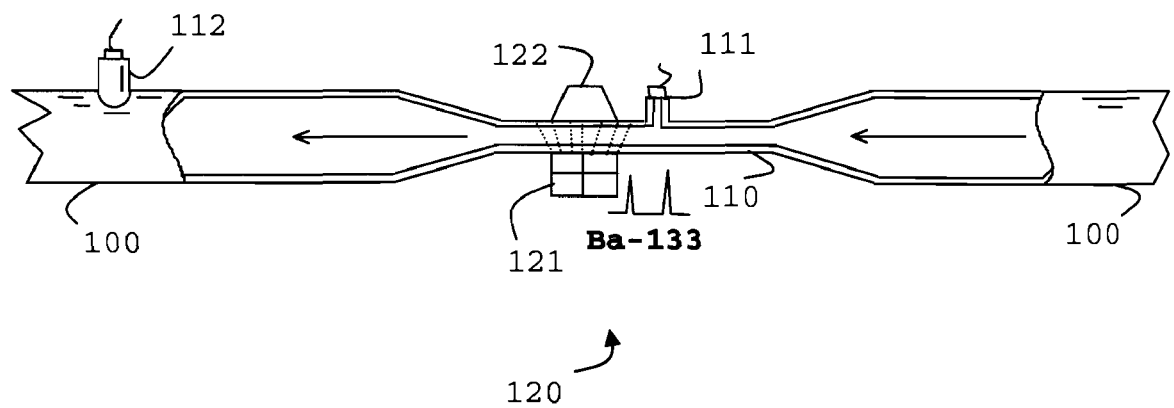
FIG. 1 is a perspective view of a section of pipe including a known Venturi flowmeter used to measure velocity and to mix gas, oil and water according to a preferred embodiment of the invention.

In FIG. 1, there is shown schematic cross-sectional view of a section of pipe 100 including a throat section or Venturi 110 used to measure hold-ups and velocity of an oil, gas and water mixture using a dual-energy densitometer 120 located within the throat section.

The densitometer 120 includes a radioactive source 121 generating a low-energy beam with a peak energy at 30 keV and a high energy beam at 356 keV using for example a Barium Ba-133 source. A receiver 122 measures the attenuation of the beams. For the purpose of the invention the beam scattering, absorption or other related beam properties may be used instead of the attenuation.

The other flow properties are calculated using the pressure gradient along the throat section 110 measured using pressure sensors or taps 111 and 112.

According to the known methods, the Dual Energy Fraction Meter (DEFM) model solves the following equations:

$$W_m^{he} = W_v^{he} \exp(-A_m^{he}) \text{ with } A_m^{he} = \alpha_w A_w^{he} + \alpha_o A_o^{he} + \alpha_g A_g^{he}$$

$$W_m^{le} = W_v^{le} \exp(-A_m^{le}) \text{ with } A_m^{le} = \alpha_w A_w^{le} + \alpha_o A_o^{le} + \alpha_g A_g^{le}$$

$$\alpha_w + \alpha_o + \alpha_g = 1 \quad [1]$$

where $\alpha_w, \alpha_o, \alpha_g$ are the unknown volumetric fractions (hold ups).

$W_m^{he}$ and $W_m^{le}$ are the (measured) count rates in the high (he) and low (le) energy windows.

$W_v^{he}$ and $W_v^{le}$ are the (calibrated) corresponding count rates in vacuum.

$A_w^{he}, A_w^{le}, A_o^{he}, A_o^{le}, A_g^{he}$ and $A_g^{le}$ are the (calibrated) attenuations in single phases.

At any energy the attenuation can be written as:

$$A = D_T \nu \rho \quad [2]$$

$D_T$ is the path length of the photons through the fluid; in the above example it is the venturi throat diameter and $\nu$ is the mass attenuation coefficient.

At a given energy, for any substance containing n different elements $$\nu = \sum_{i=1}^{n} \beta_i \nu_i \quad [3]$$

where $\beta_i$ and $\nu_i$ are the mass fraction and the mass attenuation coefficient of the i-th element respectively.

The attenuation coefficient of a known molecule or composition can be derived from experiment and/or calculations using for example the tables and values provided by the United States National Institute of Standards and Technology (NIST)

Figure 2A:
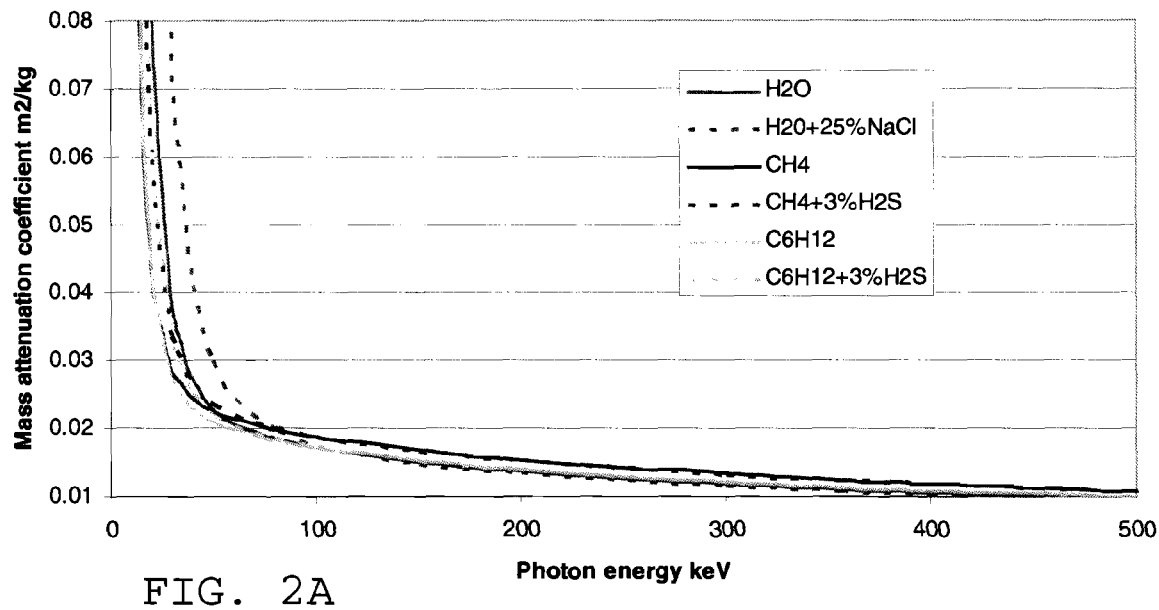

The NIST plot of FIG. 2A shows the variation in the mass attenuation coefficient at various energies and for different compositions (the water values are the extremes of what can be expected in the oil field (pure water to saturated with NaCL)). The oil values are C6H12 and C6H12 with dissolved hydrogen sulfate H2S. Methane is presented as pure gas and contaminated with H2S. In all three cases is the pure material shown as a solid line and the contaminated mixture as dashed line.

The plot shows that at energies >~80 kev the mass attenuation coefficient is a constant and almost independent of composition.

Hence at photon energies above 80 or 100 keV (Compton scattering range), the densitometer measures the density of the mixture flowing through the flowmeter.

Figure 2B:
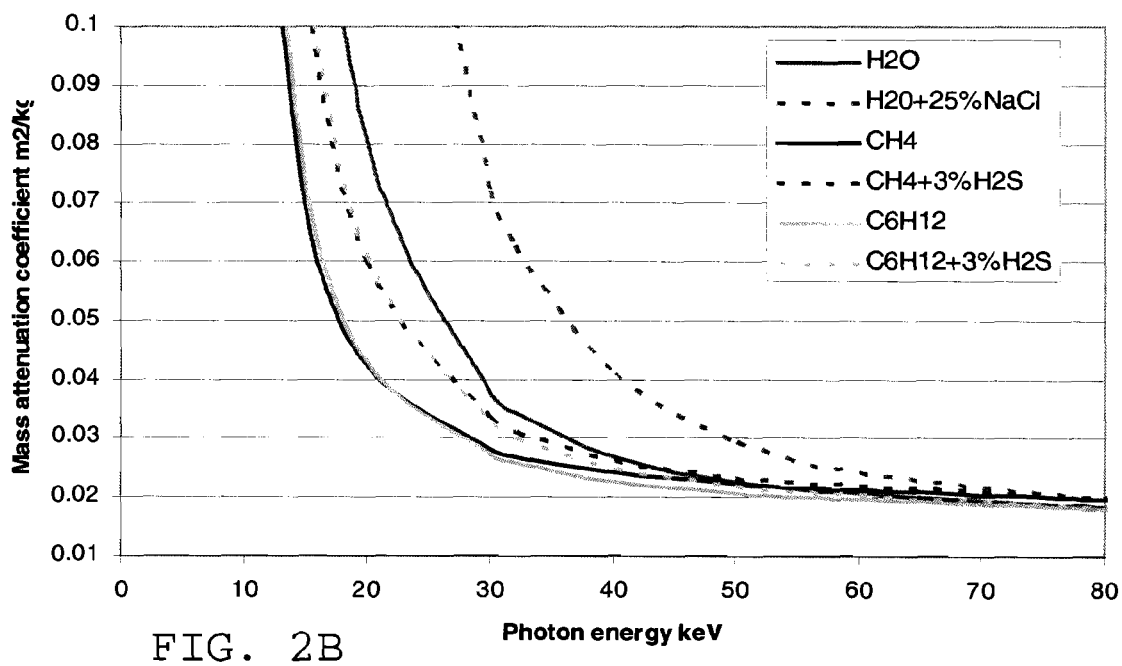

At energies <~80 or, more preferably, 50 keV (Photoelectric effect range) the mass attenuation coefficient is composition sensitive as shown in left hand side of FIG. 2A and again magnified in FIG. 2B Using two energies, the basic model to be solved in the presence of water, oil and gas is using the same notation as above $$W_m^{he} = W_v^{he} \exp[-D_T(\alpha_w \nu_w^{he} \rho_w + \alpha_o \nu_o^{he} \rho_o + \alpha_g \nu_g^{he} \rho_g)]$$

$$W_m^{le} = W_v^{le} \exp[-D_T(\alpha_w \nu_w^{le} \rho_w + \alpha_o \nu_o^{le} \rho_o + \alpha_g \nu_g^{le} \rho_g)]$$

$$\alpha_w + \alpha_o + \alpha_g = 1 \quad [1B]$$

which represents 3 equations in 3 unknown hold-ups $\alpha_w, \alpha_o$, and $\alpha_g$.

Following known methods, the model represented by [1B] are solved assuming that the single phase densities are known and that the mass attenuation coefficients can be determined from the composition or by a calibration.

It is now assumed that the composition of the flow has changed. In the following first example in accordance with the invention an additional fourth phase or component has been added to the flow.

In this case the model changes to $$W_m^{he} = W_v^{he} \exp[-D_T(\alpha_w \nu_w^{he} \rho_w + \alpha_o \nu_o^{he} \rho_o + \alpha_g \nu_g^{he} \rho_g + \alpha_x \nu_x^{he} \rho_x)]$$

$$W_m^{le} = W_v^{le} \exp[-D_T(\alpha_w \nu_w^{le} \rho_w + \alpha_o \nu_o^{le} \rho_o + \alpha_g \nu_g^{le} \rho_g + \alpha_x \nu_x^{le} \rho_x)]$$

$$\alpha_w + \alpha_o + \alpha_g + \alpha_x = 1 \quad [1C]$$

The model now includes 3 equations in 4 unknowns $\alpha_w, \alpha_o, \alpha_g$ and $\alpha_x$.

According to the invention this model can be solved when using values derived independently through prior knowledge and/or parallel measurement.

In the present example the prior knowledge include additional information relating directly a hold-up or indirectly through the knowledge of the value of a function of one or more hold-ups:

1) $\alpha_w = 0$: i.e. wlr=0
2) $\alpha_w = 1$: i.e. wlr=1
3) $\alpha_g$ known: i.e. know the gas—volume—fraction 4) wlr known: $\alpha_w/(\alpha_w+\alpha_o)$ known 5) one of $\alpha_i$ known or a $f(\alpha_i)$ known This can be applied for any fluid composition that gives a large change (with percentage of presence) in the mass attenuation coefficient.

In for example the case of H2S and knowing that the water liquid ration wlr=0 then the above example can be used to measure the quantity of $H_2S$ and track its changes.

Figure 3:
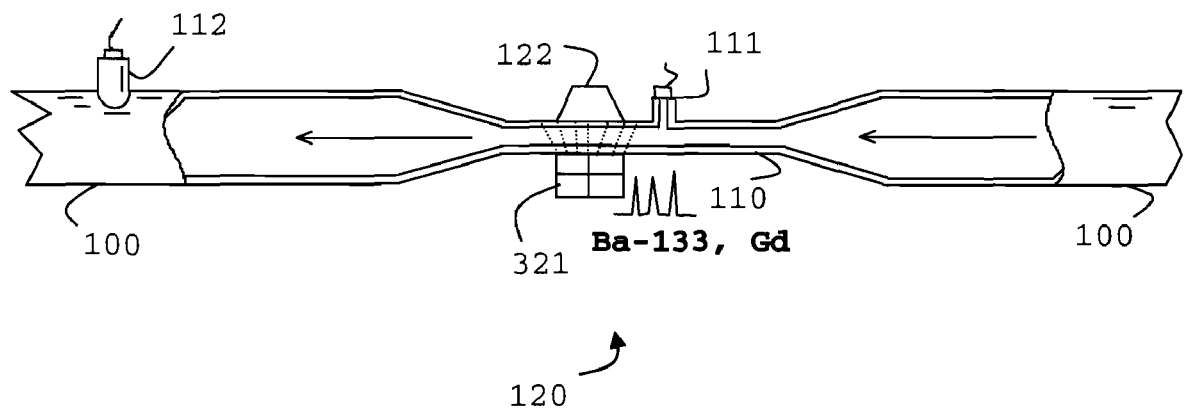
FIG. 3 is a variant of FIG. 1 modified in accordance with an aspect of the invention.

However the invention can be extended using a modified densitometer as shown in FIG. 3. Most elements of FIG. 3 are identical or similar to those shown in FIG. 1 and are hence denoted using the same numerals. A modified radio source 321 however is used generating photon rays at three different energy levels, two of which are preferably within the Photoelectric effect range. Possible radionuclides that could enhance the emission spectrum of the source include Gadolinium with peak emissions at 42 keV and 104 keV. Other possibly useful radioisotopes are isotopes of Americium, Cobalt and Caesium.

In this example, the model equation (assuming the presence of four components) change to $$W_m^{he} = W_v^{he} \exp[-D_T(\alpha_w v_w^{he}\rho_w + \alpha_o v_o^{he}\rho_o + \alpha_g v_g^{he}\rho_g + \alpha_x v_x^{he}\rho_x)]$$

$$W_m^{le1} = W_v^{le1} \exp[-D_T(\alpha_w v_w^{le1}\rho_w + \alpha_o v_o^{le1}\rho_o + \alpha_g v_g^{le1}\rho_g + \alpha_x v_x^{le2}\rho_x)]$$

$$W_m^{le2} = W_v^{le2} \exp[-D_T(\alpha_w v_w^{le2}\rho_w + \alpha_o v_o^{le2}\rho_o + \alpha_g v_g^{le2}\rho_g + \alpha_x v_x^{le2}\rho_x)]$$

$$\alpha_w + \alpha_o + \alpha_g + \alpha_x = 1 \quad [1D]$$

The three energy measurement provides a system of four equation with four unknowns.

In principle the proposed method can be extended to n X-ray or gamma-ray energies and n+1 unknown components as because the sum of the unknown fractions is 1 by definition.

The invention claimed is:

1. A method for identifying changes in composition in a flow containing an oil/hydrocarbon gas fluid mixture, comprising the steps of receiving prior knowledge of a holdup of any one of the oil, hydrocarbon gas or water in the mixture or a function thereof;

measuring the respective holdups of any two of the gas, oil and water;

performing measurements with a dual-energy source to determine attenuation or scattering of high energy photons passing through the mixture; and processing the prior knowledge, the holdup measurements and the attenuation or scattering measurements to detect the presence and/or concentration of a hetero-component in the mixture.

2. The method of claim 1, using photons with peak energies in the range of 10 keV to 80 keV and 80 keV to 100 MeV.

3. The method of claim 1, using photons with at least two peak energies in the range of 10 keV to 80 keV.

4. The method of claim 1, wherein the holdups are measured using a Venturi meter.

5. The method of claim 1, wherein the fluid mixture is hydrocarbon well production fluid.

6. The method of claim 1, wherein the hetero-component is hydrogen sulfide (H2S).

7. The method of claim 1, wherein the hetero-component is the salt-content of the water.

8. Flowmeter including a Venturi section and a dual-energy densitometer, adapted for a method in accordance with claim 1.

* * * * *